United States Patent [19]
Czeizler Zaharia

[11] Patent Number: 5,951,996
[45] Date of Patent: Sep. 14, 1999

[54] TREATMENT OF CHRONIC DIFFUSE GI BLEEDING WITH ERYTHROPOIETIN

[76] Inventor: Veronica L. Czeizler Zaharia, 237 E. 20th St., New York, N.Y. 10003

[21] Appl. No.: 09/018,815

[22] Filed: Feb. 4, 1998

[51] Int. Cl.$^6$ ............................. A61F 2/02; C07K 14/505
[52] U.S. Cl. ............................................ 424/423; 424/350
[58] Field of Search ...................... 424/430; 530/388.23, 530/350

[56] References Cited

U.S. PATENT DOCUMENTS

| | | | |
|---|---|---|---|
| 5,399,551 | 3/1995 | Ise et al. | 514/8 |
| 5,554,380 | 9/1996 | Cuca et al. | 424/441 |
| 5,670,163 | 9/1997 | Cuca et al. | 424/439 |

OTHER PUBLICATIONS

Erythropoietin and Anemia of Gastrointestinal Bleeding in a Jehovah's Witness, Jorge P. Ferrer et al., Annals of Internal Medicine, vol. 112, No. 7, p. 552, Apr. 1990.

Search Result—1; Subject: Erythropoietin and Gastrointestinal Hemmorrhage, Jan. 13, 1998, pp. 1–5, Journal Article.

*Primary Examiner*—Carlos A. Azpuru
*Attorney, Agent, or Firm*—Gottlieb, Rackman & Reisman, P.C.

[57] ABSTRACT

A method for the treatment of diffused GI bleeding by the subcutaneous administration of erythropoietin. The method is suitable for patients with radiation induced proctitis or diffused angiodysplasia of the colon, and makes unnecessary the need for the removal of portions of the GI track. Continuation of the administration of erythropoietin is necessary to avoid subsequent hematochesia and a drop in Hgb/Hcrt. The invention provides a conservative treatment for diffused GI bleeding which works on extensive areas of the GI mucosa. The treatment (1) stops the chronic diffuse GI bleeding, (2) eliminates the need for further transfusions, with its attendant complications (3) treatment is as an outpatient without the need for surgery, (4) the patient is returned to an excellent quality of life, (5) there is a major saving to the health industry, and (6) there are no observed side effects.

15 Claims, No Drawings

TREATMENT OF CHRONIC DIFFUSE GI BLEEDING WITH ERYTHROPOIETIN

FIELD OF THE INVENTION

This invention relates to a novel use for the pharmaceutical compound erythropoietin. The invention further relates to methods for controlling bleeding of the gastrointestinal tract.

BACKGROUND OF THE INVENTION

Diffuse GI (gastrointestinal) bleeding is a major medical problem following radiation treatments. Angiodysplasia of the intestine is now considered the most frequent cause of major colorectal bleeding being more frequent than diverticular bleeding. Radiation proctosigmoiditis has been studied by Gilinsky et. al. (1983) who found that 35% of patients had moderate GI bleeding and 20% had appreciable bleeding with a significant number of these patients needing operation to remove the affected bowel segment.

Patients suffering from diffuse GI bleeding are currently treated with repeated blood transfusions and surgical resection of the involved segment of the GI tract. A major problem with surgical treatment, however, is that a bowel that has been irradiated does not heal well and the breakdown of a suture line after surgery is a frequent complication, requiring further surgery and the removal of more of the bowel. Also, the dense adhesions that developed following radiation to the pelvis often make it difficult to delineate normal anatomy from pathology, and surgery therefore results in the removal of more bowel than is strictly necessary. In angiodysplasia of the colon, it sometimes is difficult to establish the exact site of bleeding. Sometimes, the small and large bowel are affected concomitantly and establishing the exact extent of resection can be very difficult for the surgeon.

Colonoscopic electro-coagulation and laser therapy are the preferred method of treatment for recurrent bleeding. The incidence of re-bleeding and the need for repeating the procedure varies from 0–34%. Surgical resection is often necessary when bleeding recurs. Occasionally re-bleeding occurs post-resection when the site of bleeding is more extensive that originally thought. In both situations presented, there is a need for a conservative treatment which should work on extensive areas of the GI mucosa.

Conservative treatment (steroid retention enemata) by administration of sulphasalazine and 5-aminosalicylic acid (mesalamine—a gastrointestinal anti-inflammatory used in the treatment of ulcerative colitis) has been tried with variable results in radiation proctitis. In cases of angiodysplasia of the intestine, the use of vasopressin infusions lead to re-bleeding in 21% of cases. Embolisation with Gelfoam has a high risk of re-infarction. These attempts at conservative treatments demonstrate that there has been a long felt need for an alternative to surgical intervention to reduce diffuse GI bleeding.

Erythropoietin (also known as procrit) is a glycoprotein hormone, thought to be produced primarily in the kidneys, which is a stimulating factor for erythropoiesis, the process by which erythrocytes (red blood cells) are formed in the bone marrow. Human erythropoietin has been produced by recombinant technology, and is known as Epoetin.

Erythropoietin is being used successfully in the treatment of anemia of chronic renal failure, anemia of cancer and in HIV patients. It is primarily used to induce production of red blood cells to combat anemia, and not to stop diffuse bleeding. Erythropoietin is known to decrease the bleeding time in uremic (kidney failure) patients. In vitro and in vivo studies on uremic patients have shown an improved platelet endothelial cell interaction, which explains the shortening of the bleeding time, but there are no studies done of the hemostatic mechanism (clotting mechanism) induced by erythropoietin on non-uremic patients. But there has been no recognition prior to the present invention of the significant limitation of GI bleeding that can be achieved by the administration of erythropoietin in uremic or non-uremic patients.

There are three reported cases of Jehovah's witnesses patients who had acute as opposed to chronic blood loss, and bleeding was localized to a small area as opposed to diffuse bleeding with critically low Hgb. The patients refused blood transfusions and were successfully treated with recombinant erythropoietin plus ferrous sulfate, folic acid and vitamin B-12 subcutaneously, which was used for its stimulating effect on the production of red blood cells.

One patient was a 66 year old woman who bled from multiple peptic ulcers. She had melena (passing of black bloody bowel movement) and sycope (passing out) with a Hcrt of 14.5%. Since she refused blood transfusion she was treated with recombinant erythropoietin 20,000 units for three doses followed by 6,500 units up to two weeks. On the 14th day, her Hcrt was 27.1%. The erythropoietin was not administered to contain bleeding, but was administered to increase the hematocrit count by boosting the red cell production only after the bleeding had stopped. Furthermore there's nothing in the publication, "Erythropoietin and Anemia of Gastrointestinal Bleeding in a Jehovah's Witness", Ann. Int. Med. 112, 552 (April 1990), that indicates that erythropoietin would stop diffuse GI bleeding. The thrust of the publication is the use of erythropoietin as a substitute for blood transfusion for Jehovah's Witnesses.

The second case was a four year old black male Jehovah's witness with hematemesis (vomiting of blood) who was found to have a 2.5 cm fundal ulcer and a Hcrt of 19.1. He was treated with Fe Dextran IV 100 mg/day, erythropoietin 50 units/kg IV. On the 8th day, his Hcrt was 22.9 and he was discharged home.

The third and last case presented in the literature was a 14 year old black male who had massive hematemesis (vomiting of blood) following esophageal dilatation for an esophageal stricture. Being a Jehovah's witness, blood transfusion was refused. He underwent surgical repair for G-E tear. The post-operative Hcrt was 14.4. Recombinant Erythropoietin 50 units/kg IV was given. Four days after surgery, his Hcrt was 25.9 and was discharged home on the 9th post-operative day tolerating oral feeding and oral iron supplementation.

In uremic patients, it is known that erythropoietin corrects the prolonged bleeding time after one week of treatment and increases the hemoglobin/Hcrt after two weeks of treatment. But this information has not been previously considered related to the problem of GI bleeding in uremic or non-uremic patients.

In uremic patients on chronic hemodialysis, it has been shown that erythropoietin alpha works on both (1) the primary hemostatic plug formation as well as (2) the coagulation phase. (1) Within the mechanism of the primary hemostatic plug formation, it increases the platelet count, the collagen dependent platelet aggregation and the ristocetin induced platelet aggregation. It produces a rise in blood and platelet serotonin content that is supposed to lead to an improved platelet-endothelial cell interaction also, serotonin produces vasoconstriction. All of these effects lead to a shortening of the bleeding time in uremic patients on chronic hemodialysis.

On the other hand, (2) erythropoietin alpha used in uremic patients on hemodialysis also worked on the coagulation phase by producing decline of the protein C, protein S and anti-thrombin III (which are natural anti-coagulants and their deficiency leads to an enhancement of the coagulation mechanism). All of the findings on uremic patients on hemodialysis provide a scientific basis for the observed effect of erythropoietin alpha in limiting GI bleeding in the non-uremic patients.

BRIEF DESCRIPTION OF THE INVENTION

In patients with chronic diffuse GI bleeding (e.g. radiation induced proctitis or diffused angiodysplasia of the colon) the treatment of the present invention comprises administration of erythropoietin, preferably subcutaneously. The invention results in the increase of hemoglobin/hematocrit (Hgb/Hcrt) to normal values and no further need for transfusion. Continuation of the administration of erythropoietin at much lower than initial doses at weekly intervals for several months is necessary to avoid hematochesia (passing of red blood through the rectum) and a drop in Hgb/Hcrt.

In the two examples presented below, recombinant Erythropoietin (1) stopped the GI bleeding, (2) no further transfusions were needed, thereby avoiding the complications of repeated transfusions (3) treatment was done as an outpatient, (4) without the need for surgery, (5) the patient returned to an excellent quality of life, (6) there was a major saving to the health industry, and (7) no side effects were noted.

The present invention therefore provides a conservative treatment which works to reduce chronic diffuse GI bleeding on extensive areas of the GI mucosa.

DETAILED DESCRIPTION OF A PREFERRED EMBODIMENT

The invention is appropriate for patients suffering from chronic severe GI bleeding with critically low Hgb/Hcrt. Treatment with recombinant erythropoietin is initiated for the purpose of stopping the GI bleeding, boosting the red blood cell production and decreasing future transfusion requirement, at the dose of 5,000 units, three times per week. When Hgb/Hcrt is stable for several days and there is no further clinical evidence of ongoing bleeding, the patient may be discharged on maintenance doses of recombinant erythropoietin which was 3,000 units, once a week. After a few weeks of lack of recurrence of bleeding, the patient is placed on 3000 units of recombinant erythropoietin injection at once a week. After treatment is initiated in accord with this invention no bleeding is noted and no further transfusion is needed, although hematochesia may recur, some drop in Hgb/Hcrt may occur, and the stool may become guaiac positive if erythropoietin treatment is dropped completely, but with complete resolution of these symptoms is erythropoietin is restarted.

EXAMPLE 1

A 65 year old black male was treated in accord with the present invention. The patient had a history of radiation proctitis secondary to radiotherapy for a prostate cancer with a string of hospital admissions for critically low Hgb/Hcrt and packed RBC transfusions prior to the initiation of erythropoietin. When first seen in consultation during one of his hospital admissions, when his Hgb was 3.5, Hcrt-12.2 and MCV 65. During the 6 months preceding the initiation of erythropoietin, 20 units of packed red blood cells (PRBC) were transfused. Two colonoscopies revealed diffused angioectasia (dilation of the small blood vessels) of the recto-sigmoid mucosa and diffused erosions and oozing of blood, consistent with radiation proctitis. Courtenemas were unsuccessful in stopping the bleeding. Repeat electrocoagulation done with a colonoscope several times were followed by rebleeding after each attempt at stopping the blood loss.

Recombinant erythropoietin 5,000 units three times a week were started. After the first week of treatment, the bleeding completely stopped. No further transfusion was needed, the patient's bleeding stopped, his Hgb came up to 13 and he felt better. The patient was however very non-compliant to continuing the treatment, he failed to return for further treatment. The patient would come once every one-two weeks and later on every four to six weeks at which time recombinant erythropoietin 5,000 units were administered subcutaneously. During the time when he was off-recombinant erythropoietin for several weeks, the rectal bleeding would recur, his Hgb would drop to about 7.0. After recombinant erythropoietin was restarted, the rectal bleeding would disappear and the Hgb/Hcrt would rise. To this date, no packed RBC were transfused after erythropoietin had been started.

EXAMPLE 2

Another patient was an 84 year old white male with multiple hospital admissions for lower GI bleeding and severe symptomatic iron deficiency anemia. For the previous two years he was admitted to the hospital every two months for packed red blood cell transfusion of 4 units. when he was first seen in consultation he was admitted to the hospital with a Hgb of 5.2 and four units of PRBC were transfused. Two months later, he was readmitted for hematochesia a Hgb of 9.0 and colonoscopy revealed diffuse colonic angiodysplasia. He was started on recombinant erythropoietin 4,000 units three times a week which he received for two weeks, followed by 4,000 units two times a week for two months after which he was maintained on 2,000 units once or twice a week, then 3000 units once a week. His Hgb has increased from 9.0 to 13.0. He was very compliant with respect to treatment and no transfusion of packed red blood cells has been used since recombinant erythropoietin was initiated. His Hgb was stable between 12.0 and 13.0 for the subsequent year with no clinical evidence of bleeding.

The two examples showed a clear benefit in using recombinant Erythropoietin to stop chronic diffuse transfusion dependent GI bleeding. In the compliant patient, there was never the decrease in Hcrt experienced by the non-compliant patient, which demonstrates the effectiveness of the treatment. There is a clear clinical benefit to using recombinant erythropoietin in stopping chronic diffused chronic GI bleeding such as diffused angiodysplasia of the colon and radiation proctitis. The recurrence of bleeding after stopping erythropoietin and the stopping of bleeding again after re-starting recombinant erythropoietin provides a conservative treatment for a bleeding condition for which there was no good treatment, conservative or surgical. Patients who are completely transfusion dependent become totally transfusion independent, as shown in the examples, there was secession of the GI bleeding, the patient was treated as an outpatient without the need for surgery, the patient returned to an excellent quality of life, there was a major saving to the health industry, and no side effects were noted. This new use of recombinant erythropoietin beyond the anemia of chronic renal failure, anemia of HIV infected patients, anemia of cancer provides a new significant medical treatment.

Although the invention has been described in terms of preferred embodiments and specific examples, it is expected that the invention may be practiced by modifications that persons skilled in this art may achieve. Accordingly the invention is to be understood as what is described in the following claims.

I claim:

1. A method for treating diffused gastrointestinal bleeding comprising administering to an individual in need of said treatment and effective dose of erythropoietin so that the symptoms of diffused gastrointestinal bleeding are significantly reduced.

2. The method for treating diffused gastrointestinal bleeding of claim 1 in which the dose of erythropoietin is administered in the form selected from the group consisting of natural erythropoietin and recombinant erythropoietin.

3. The method for treating diffuse gastrointestinal bleeding of claim 2, in which the erythropoietin is administered in dosages between 15000 and 30000 units per week until the bleeding stops, and continuing to administer erythropoietin on a reduced basis thereafter.

4. The method for treating chronic diffuse gastrointestinal bleeding of claim 2, in which the erythropoietin is administered in dosages up to 60,000 units per week until the bleeding stops, and continuing to administer erythropoietin on a reduced basis thereafter.

5. The method for treating diffused gastrointestinal bleeding of claim 3, wherein the continued administration of erythropoietin takes place weekly or biweekly.

6. The method for treating diffused gastrointestinal bleeding of claim 1, wherein the bleeding is a result of radiation induced proctitis or diffused angiodysplasia of the colon.

7. A method for treating diffused gastrointestinal bleeding in a patient suffering from severe GI bleeding with critically low Hgb/Hcrt comprising administering to an individual in need of said treatment and effective dose of erythropoietin so that the Hgb/Hcrt is stable for several days and there is no further clinical evidence of ongoing bleeding, discharging the patient on maintenance doses of recombinant erythropoietin.

8. The method for treating diffused gastrointestinal bleeding in a patient suffering from severe GI bleeding of claim 7, in which the administering is subcutaneous.

9. The method for treating diffused gastrointestinal bleeding in a patient suffering from severe GI bleeding of claim 7, in which the amount administered is a dose of approximately 15,000 units per week.

10. The method for treating diffused gastrointestinal bleeding in a patient suffering from severe GI bleeding of claim 7, in which the maintenance dose is approximately 9000–15,000 units per week.

11. The method for treating diffused gastrointestinal bleeding in a patient suffering from severe GI bleeding of claim 8, comprising the further step of placing the patient on dosages of recombinant erythropoietin injection amounting to 5000 to 10000 units per week.

12. The method for treating diffused gastrointestinal bleeding in a patient suffering from severe GI bleeding of claim 8, comprising the further step of placing the patient on dosages of recombinant erythropoietin injection of approximately 20,000 units per month.

13. The method for treating diffused gastrointestinal bleeding in a patient suffering from severe GI bleeding of claim 7, wherein the amount administered is a dose of approximately 15,000 units per week, the maintenance dose is 9,000–15,000 per week, and the patient is subsequently placed on dosages of recombinant erythropoietin injection at approximately one month intervals.

14. A method for treating chronic diffused bleeding comprising administering to an individual in need of said treatment and effective dose of erythropoietin so that the symptoms of chronic diffused bleeding are significantly reduced.

15. A method for treating chronic diffused bleeding in a patient suffering from severe chronic bleeding with critically low Hgb/Hcrt comprising administering to an individual in need of said treatment and effective dose of erythropoietin so that the Hgb/Hcrt is stable for several days and there is no further clinical evidence of ongoing bleeding, discharging the patient on maintenance doses of recombinant erythropoietin.

* * * * *